US 6,661,873 B2

United States Patent
Jabri et al.

(10) Patent No.: US 6,661,873 B2
(45) Date of Patent: Dec. 9, 2003

(54) MOTION ARTIFACTS REDUCTION ALGORITHM FOR TWO-EXPOSURE DUAL-ENERGY RADIOGRAPHY

(75) Inventors: Kadri N. Jabri, Waukesha, WI (US); Gopal B. Avinash, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 35 days.

(21) Appl. No.: 10/058,616

(22) Filed: Jan. 28, 2002

(65) Prior Publication Data

US 2003/0142787 A1 Jul. 31, 2003

(51) Int. Cl.$^7$ ................................................. H05G 1/00
(52) U.S. Cl. ........................... 378/98.11; 378/5; 378/62
(58) Field of Search ............................ 378/5, 62, 98.8, 378/98.9, 98.11, 98.12

(56) References Cited

U.S. PATENT DOCUMENTS

| 5,216,252 A | * | 6/1993 | Boone et al. | ............ 250/486.1 |
| 5,451,793 A | * | 9/1995 | Boone | ..................... 250/486.1 |
| 6,205,348 B1 | | 3/2001 | Giger et al. | ................. 600/407 |
| 6,343,111 B1 | * | 1/2002 | Avinash et al. | .......... 378/98.11 |
| 2002/0186872 A1 | * | 12/2002 | Avinash et al. | ............. 382/132 |

* cited by examiner

Primary Examiner—David V. Bruce
(74) Attorney, Agent, or Firm—Fletcher Yoder

(57) ABSTRACT

The present technique provides a variety of processing schemes for decomposing soft tissue and bone images more accurately from low and high-energy images acquired from an imaging system, such as a dual-energy digital radiography system using flat-panel technology. In particular, a pre-decomposition process is provided for spatially matching, or registering, low and high-energy images using warping registration prior to dual energy image decomposition, which creates the soft tissue and bone images. Accordingly, the pre-decomposition process reduces motion artifacts between the low and high-energy images, thereby improving image clarity of the decomposed soft tissue and bone images.

56 Claims, 12 Drawing Sheets

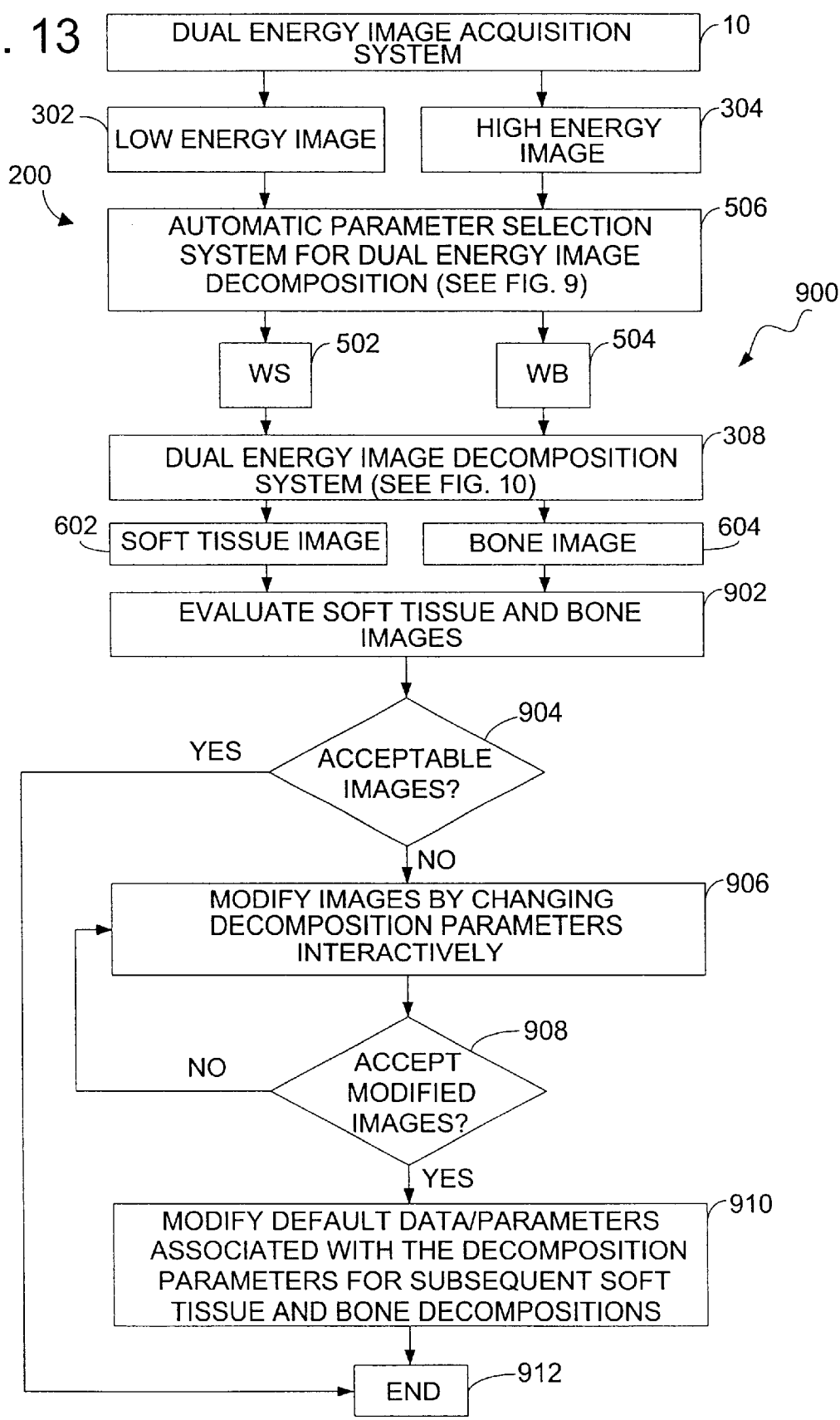

MOTION ARTIFACTS REDUCTION ALGORITHM FOR TWO-EXPOSURE DUAL-ENERGY RADIOGRAPHY

BACKGROUND OF THE INVENTION

The present invention relates generally to imaging systems, such as radiographic systems, and more particularly, to processing techniques for dual-energy radiography. Even more particularly, the present invention relates to a system and method for reducing motion artifacts in soft tissue and bone images decomposed from low and high-energy images acquired from an imaging system, such as a dual-energy digital radiography system using flat-panel technology.

Medical diagnostic and imaging systems are ubiquitous in modern health care facilities. Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, and so forth. Such systems provide invaluable tools for identifying, diagnosing and treating physical conditions and greatly reduce the need for surgical diagnostic intervention. In many instances, these modalities complement one another and offer the physician a range of techniques for imaging particular types of tissue, organs, physiological systems, and so forth.

Digital imaging systems are becoming increasingly widespread for producing digital data that can be reconstructed into useful radiographic images. In one application of a digital imaging system, radiation from a source is directed toward a subject, typically a patient in a medical diagnostic application, and a portion of the radiation passes through the subject and impacts a detector. The surface of the detector converts the radiation to light photons, which are sensed. The detector is divided into an array of discrete picture elements or pixels, and encodes output signals based upon the quantity or intensity of the radiation impacting each pixel region. Because the radiation intensity is altered as the radiation passes through the subject, the images reconstructed based upon the output signals may provide a projection of tissues and other features similar to those available through conventional photographic film techniques. In use, the signals generated at the pixel locations of the detector are sampled and digitized. The digital values are transmitted to processing circuitry where they are filtered, scaled, and further processed to produce the image data set. The data set may then be used to reconstruct the resulting image, to display the image, such as on a computer monitor, to transfer the image to conventional photographic film, and so forth.

In dual-energy imaging systems, such as dual-energy digital radiography systems, the system acquires two images of a desired anatomical region of a patient at different energy levels, such as low and high energy levels. The two images are then used to decompose the anatomy and to create soft tissue and bone images of the desired anatomical region. The two images are generally decomposed according to the dual-energy decomposition equations:

$$IS = IH/IL^{WS}$$

$$IB = IH/IL^{WB}$$

where IS represents the soft tissue image, IB represents the bone image, IH represents the high-energy image, IL represents the low-energy image, WS is the soft tissue decomposition parameter, WB is the bone decomposition parameter, and $0 < WS < WB < 1$. The soft tissue and bone decomposition parameters must be selected carefully to provide acceptable dual-energy image quality. Unfortunately, the soft tissue and bone decomposition parameters may be functions of several image and techniques variables, thereby complicating the selection of these parameters. Moreover, the decomposed images typically have significant noise, contrast artifacts, and motion artifacts, which degrade the images and reduce the value of the images for medical diagnosis. These artifacts are generally mitigated by post-decomposition processing techniques, yet the decomposed images still exhibit significant artifacts.

At relatively attenuated regions of the image, the foregoing dual-energy decomposition equations produce relatively noisy decomposed images. For example, during a low-dose clinical data acquisition, the computationally efficient decomposition equations amplify noise and produce very noisy decomposed images at highly attenuated regions of the image. Existing noise reduction techniques mitigate noise in the images after decomposition by the foregoing decomposition equations. However, the foregoing decomposition equations tend to amplify noise in the images, and the existing noise reduction techniques fail to mitigate the noise adequately.

Artifacts also may arise in the decomposed images due to anatomical movement between the two image acquisitions. Although the two images may be acquired over a relatively short time interval, such as 100–200 ms, these motion artifacts may significantly degrade the quality of the decomposed images. For chest radiography, the motion artifacts manifest as residual rib contrast, which causes rib structure to be visible in the soft tissue image. The residual rib structure, which is present in about 30 percent of acquisitions, decreases the conspicuity of lung pathology and essentially defeats the purpose of generating soft tissue lung images by dual-energy imaging. Traditional methods to correct for motion artifacts are relatively ineffective for dual-energy imaging, because the dual-energy images have significantly different local contrasts.

Accordingly, a technique is needed for reducing noise, contrast, and motion artifacts in the images decomposed from a dual-energy imaging system, such as a dual-energy digital radiography imaging system. A technique is also needed for selecting parameters for the dual-energy decomposition process. It also would be advantageous to automate various aspects of the image processing and decomposition process, including the selection of decomposition parameters.

SUMMARY OF THE INVENTION

The present technique provides a variety of processing schemes for decomposing soft tissue and bone images more accurately from low and high-energy images acquired from an imaging system, such as a dual-energy digital radiography system using flat-panel technology. In particular, a pre-decomposition process is provided for spatially matching, or registering, low and high-energy images using warping registration prior to dual energy image decomposition, which creates the soft tissue and bone images. Accordingly, the pre-decomposition process reduces motion artifacts between the low and high-energy images, thereby improving image clarity of the decomposed soft tissue and bone images.

BRIEF DESCRIPTION OF THE DRAWINGS

The foregoing and other advantages and features of the invention will become apparent upon reading the following detailed description and upon reference to the drawings in which:

FIG. 13 is a flow chart illustrating an exemplary post-decomposition processing scheme for enhancing the decomposed soft tissue and bone images and for modifying decomposition parameter data based on a modification of the soft tissue and bone images.

DETAILED DESCRIPTION OF SPECIFIC EMBODIMENTS

Figure 1:
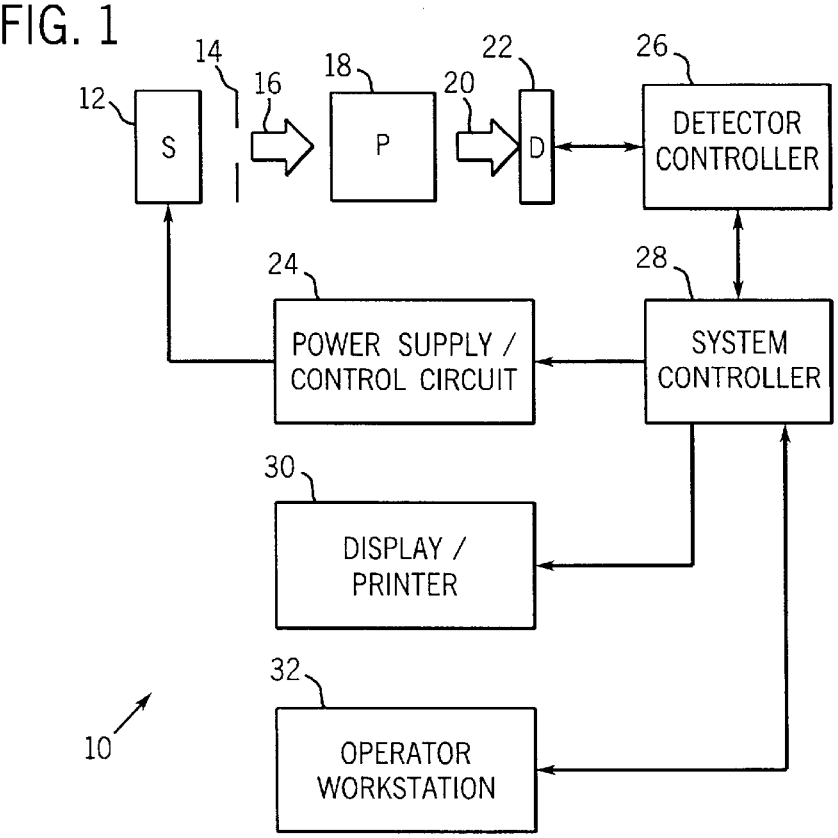
FIG. 1 is a diagrammatical overview of a digital X-ray imaging system in which the present technique may be utilized.

FIG. 1 illustrates diagrammatically an imaging system 10 for acquiring and processing discrete pixel image data. In the illustrated embodiment, system 10 is a digital X-ray system designed both to acquire original image data and to process the image data for display in accordance with the present technique. For example, the system 10 may acquire multiple images of a desired anatomy over a short time interval for comparison and processing, such as high and low-energy image exposures used for a dual-energy decomposition system. Accordingly, the system 10 may embody a dual-energy digital X-ray system, which is operable to decompose high and low-energy image exposures into soft tissue and bone images for further analysis of the desired anatomy. In the embodiment illustrated in FIG. 1, imaging system 10 includes a source of X-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital X-ray detector, represented generally at reference numeral 22. As described more fully below, detector 22 converts the X-ray photons received on its surface to lower energy photons, and subsequently to electric signals, which are acquired and processed to reconstruct an image of the features within the subject.

Source 12 is controlled by a power supply control circuit 24, which furnishes both power, and control signals for examination sequences. Moreover, detector 22 is coupled to a detector controller 26, which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
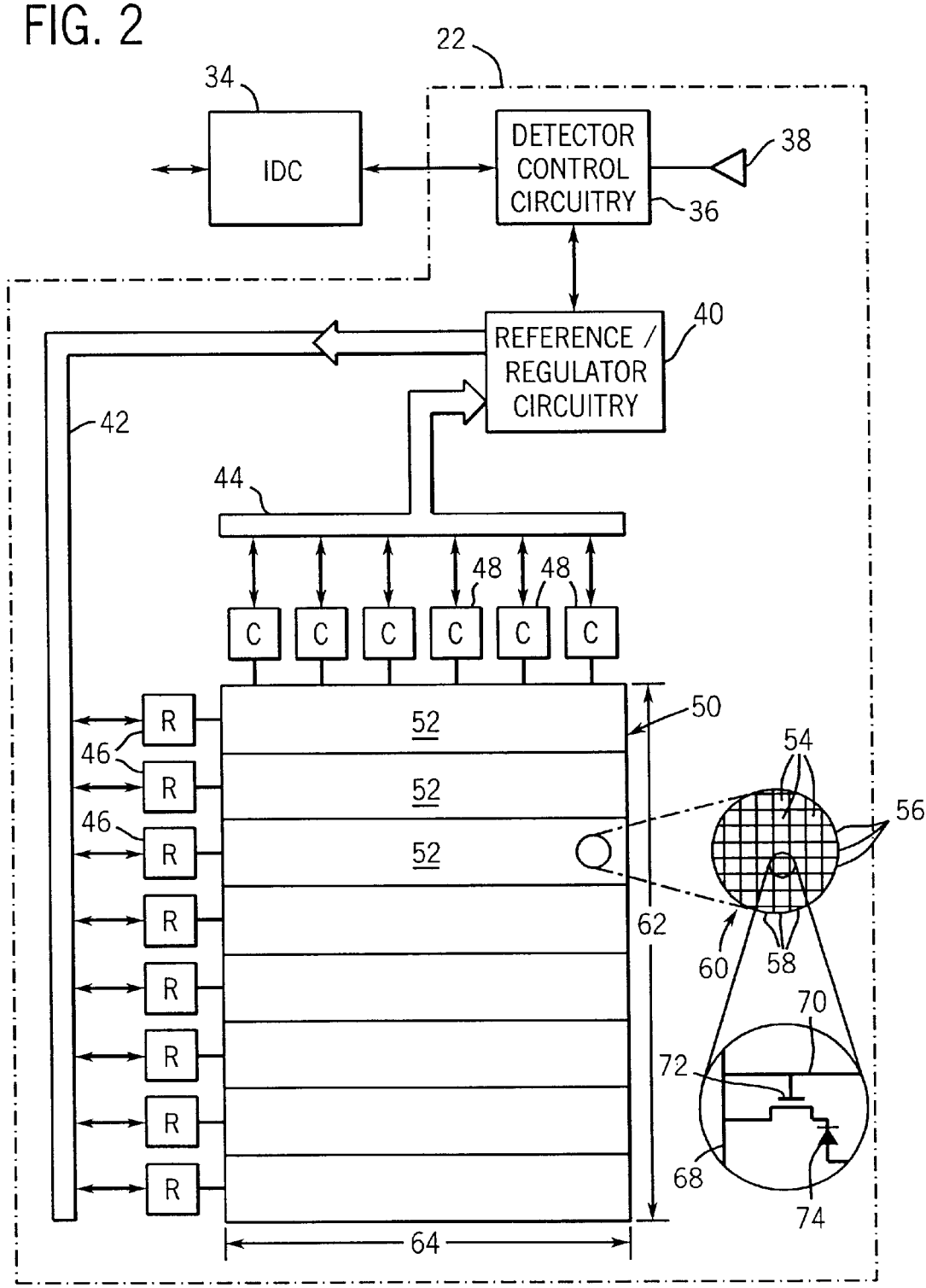
FIG. 2 is a diagrammatical representation of the functional circuitry in a detector of the system of FIG. 1 that is adapted to produce image data for reconstruction.

FIG. 2 is a diagrammatical representation of functional components of digital detector 22. FIG. 2 also represents an imaging detector controller or IDC 34, which will typically be configured within detector controller 26. IDC 34 includes a CPU or digital signal processor, as well as memory circuits for commanding acquisition of sensed signals from the detector. IDC 34 is coupled via two-way fiber optic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In a present embodiment, detector 22 consists of a scintillator that converts X-ray photons received on the detector surface during examinations to lower energy (light) photons. An array of photo detectors then converts the light photons to electrical signals, which are representative of the number of photons or the intensity of radiation impacting individual pixel regions of the detector surface. Readout electronics convert the resulting analog signals to digital values that can be processed, stored, and displayed, such as in a display 30 or a workstation 32 following reconstruction of the image.

In a present form, the array of photo detectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and an electrode of each column is connected to readout electronics.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector. In the present technique, image acquisition rate is increased by employing a partial readout of the detector 22.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64. Again, as described below, the present technique allows an enhanced number of pixels to be read out via the row and column drivers and readout electronics.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode 74 may be accessed via readout electronics 48, and converted to digital signals for subsequent processing and image reconstruction. Thus, an entire row of pixels in the array is controlled simultaneously when the scan line attached to the gates of all the transistors of pixels on that row is activated. Consequently, each of the pixels in that particular row is connected to a data line, through a switch, which is used by the readout electronics to restore the charge to the photodiode 74.

It should be noted that as the charge is restored to all the pixels in one row simultaneously by each of the associated dedicated readout channels, the readout electronics is converting the measurements from the previous row from an analog voltage to a digital value. Furthermore, the readout electronics are transferring the digital values from two previous rows to the acquisition subsystem, which will perform some processing prior to displaying a diagnostic image on a monitor or writing it to film. Thus, the read out electronics are performing three functions simultaneously: measuring or restoring the charge for the pixels in a particular row, converting the data for pixels in the previous row, and transferring the converted data for the pixels in a twice previous row.

Figure 3:
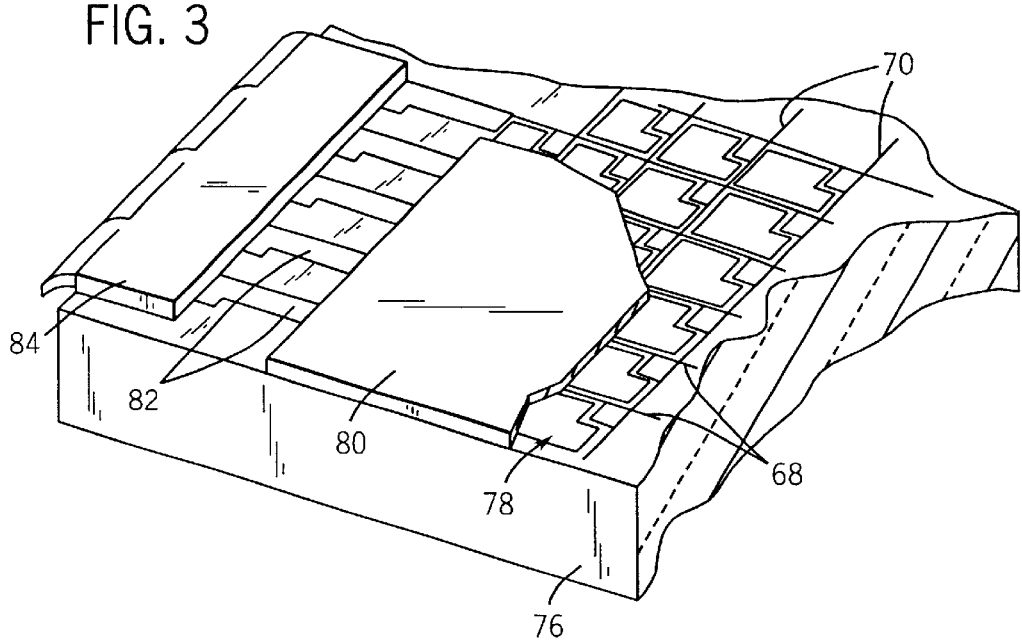
FIG. 3 is a partial sectional view illustrating an exemplary detector structure for producing the image data.

FIG. 3 generally represents an exemplary physical arrangement of the components illustrated diagrammatically in FIG. 2. As shown in FIG. 3, the detector may include a glass substrate 76 on which the components described below are disposed. Column electrodes 68 and row electrodes 70 are provided on the substrate, and an amorphous silicon flat panel array 78 is defined, including the thin film transistors and photodiodes described above. A scintillator 80 is provided over the amorphous silicon array for receiving radiation during examination sequences as described above. Contact fingers 82 are formed for communicating signals to and from the column and row electrodes, and contact leads 84 are provided for communicating the signals between the contact fingers and external circuitry.

It should be noted that the particular configuration of the detector panel 22, and the subdivision of the panel into rows and columns driven by row and column drivers is subject to various alternate configurations. In particular, more or fewer row and column drivers may be used, and detector panels having various matrix dimensions may thereby be defined. The detector panel 22 may be further subdivided into regions of multiple sections, such as along a vertical or horizontal centerline.

It should be further noted that the readout electronics in the detector generally employ a pipeline-type architecture. For example, as the charge is restored to all the pixels in a particular row simultaneously by each of the associated dedicated readout channels, the readout electronics convert the measurements from the previous row from an analog signal to a digital signal. Concurrently, the readout electronics transfer the measured digital values from two previous rows to the data acquisition subsystem. The data acquisition subsystem typically performs some processing prior to displaying a diagnostic image on a display. Thus, the readout electronics in the present technique perform three functions simultaneously.

Figure 4:
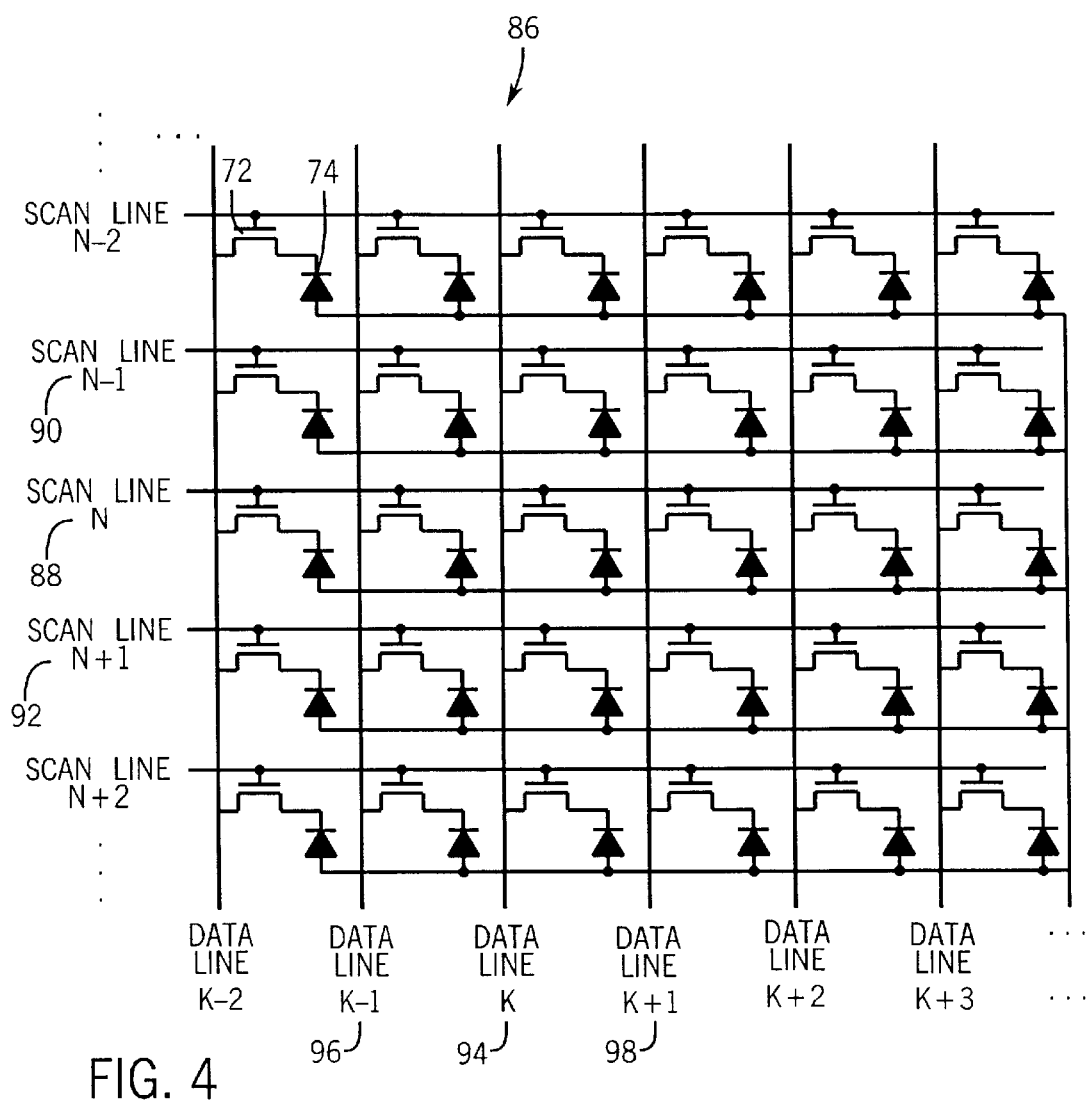
FIG. 4 is a circuit schematic illustrating rows and columns of pixels in an exemplary detector.

FIG. 4 illustrates an array of pixels 86 located on an exemplary detector having a plurality of column lines and row lines. As illustrated by the array of pixels 86, each pixel comprises the transistor 72 and the photodiode 74. It should be noted that the array is made up of a plurality of scan lines 88, 90, 92 and a plurality of data lines 94, 96 and 98. The scan lines 88, 90, 92 represent rows of pixels scanned during the imaging process. Similarly, the data lines 94, 96 and 98 represent the columns of pixels through which data is transmitted to a data acquisition system. As can be appreciated by those skilled in the art, the scan lines typically recharge the photodiode and measure the amount of charge displaced. The column or data lines typically transmit the data from each row of pixels to the data acquisition system.

As illustrated, scan line 88 (denoted N in FIG. 4) is coupled to each one of the pixels in that specific row. Additionally, scan line 88 is coupled to each of one of the data lines. For example, scan line 88 is coupled to data line 94 (denoted K in FIG. 4) and data line 98 (K+1). Similarly, each one of the data lines is coupled to each one of the scan lines. Thus, as illustrated for the array of pixels 86, scan line 88 (N), scan line 90 (N−1), and scan line 92 (N+1) are coupled to data line 94 (K), data line 96 (K−1), and data line 98 (K+1) and so on. It should be understood that each data line is typically coupled to one specific column of pixels and each scan line is coupled to one specific row of pixels. Additionally, although in the present embodiment of FIG. 4, 25 pixels are illustrated, it should be noted that additional pixels may, of course, be incorporated in the pixel array.

Figure 5:
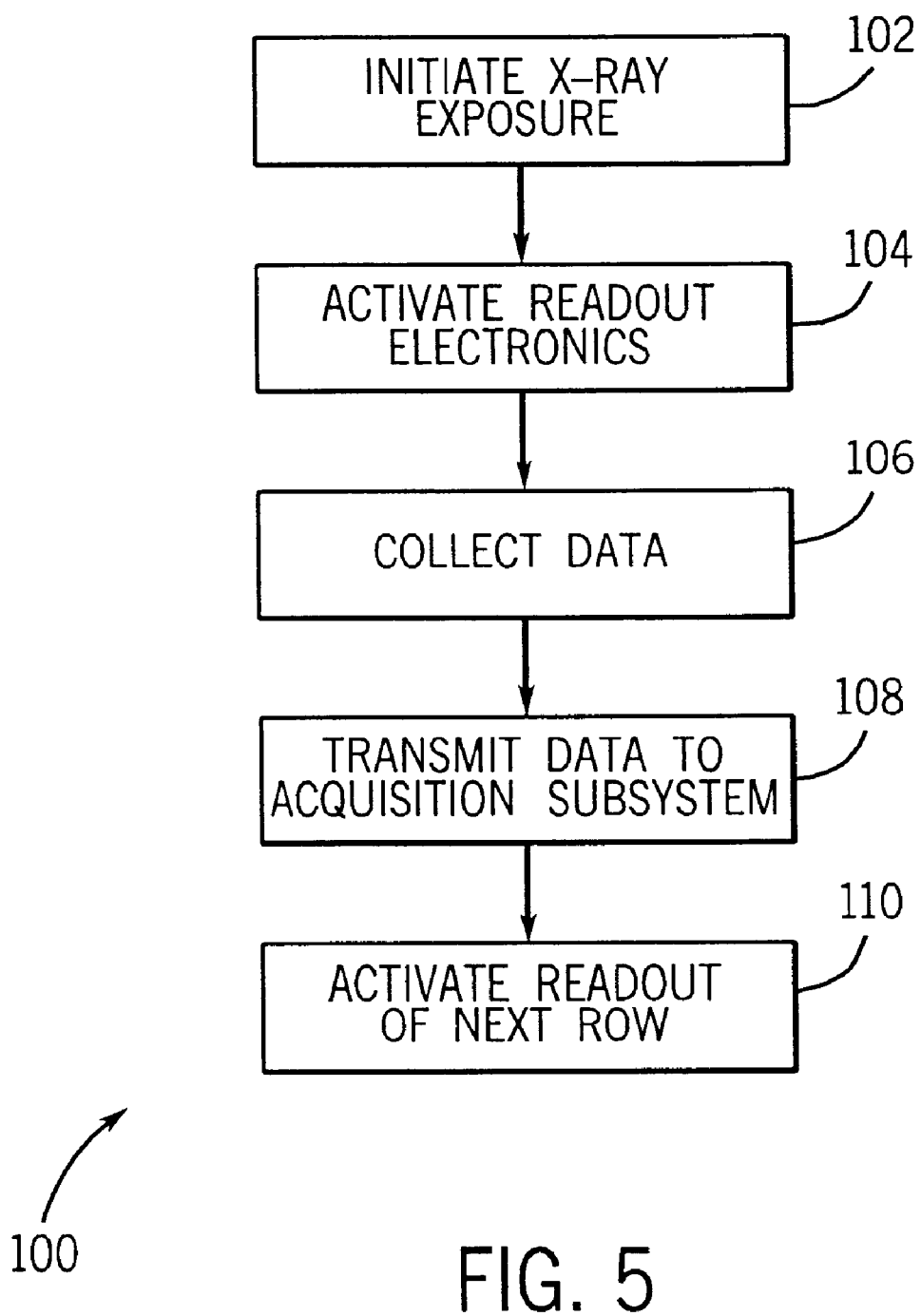
FIG. 5 is a flowchart representing a method of operating an exemplary imaging system for providing image data.

Turning to FIG. 5, a flowchart is represented illustrating a method 100 for operating an imaging system of the type described above. Initially, an X-ray exposure is initiated by an operator, as represented by step 102. Once an X-ray exposure is taken the readout electronics within the detector 22 are activated, as indicated by step 104. As mentioned above, an exposure is taken of a patient, whereby X-rays are transmitted through the patient and received by the detector. The array of pixels 86 typically measures the attenuation of the X-rays received by the detector 22, via the readout electronics provided within each individual pixel. The readout electronics typically collect data utilizing circuitry associated with each of the pixels, as indicated by step 106. Once the data are collected for a particular row of pixels, the data are transmitted to a data acquisition subsystem as indicated by step 108. Once data from one specific row of pixels is transmitted to the data acquisition subsystem, the next row of pixels is scanned and read. Thus, the readout of the next row of pixels is activated, as indicated by step 110. It should be understood that this process continues until the detector 22, and more particularly all the pixels, are read out. Subsequently, the collected data are processed and ultimately used to reconstruct an image of the exposure area.

As mentioned above, the digital x-ray system 10 may be used to acquire high and low-energy image exposures, which may be decomposed into soft tissue and bone images for detailed analysis of the desired anatomy. Accordingly, a process 200 for dual-energy image acquisition and processing is illustrated with reference to FIG. 6, which illustrates the general processing chain that is further illustrated with reference to FIGS. 7–12. As illustrated, the process 200 proceeds by initiating the dual-energy imaging system, such as the digital x-ray system 10 illustrated in FIG. 1 (block 202). The process 200 then proceeds to acquire low and high-energy images of a desired anatomy, such as chest images (block 204). The process 200 may then process the low and high-energy images prior to dual-energy decomposition, as further illustrated by FIGS. 7–8 (block 206). For example, the process 200 may perform a variety of motion correction, noise reduction, and display processing to provide higher quality images. The process 200 then proceeds to decompose the low and high-energy images into soft tissue and bone images, as further illustrated by FIG. 10 (block 208). The process 200 may then perform post-decomposition processing on the soft tissue and bone images (block 210). For example, the process 200 may perform a variety of motion correction, noise reduction, and display processing to provide higher quality images. The process 200 then proceeds to display the soft tissue and bone images for analysis by a physician (block 212).

Figure 6:
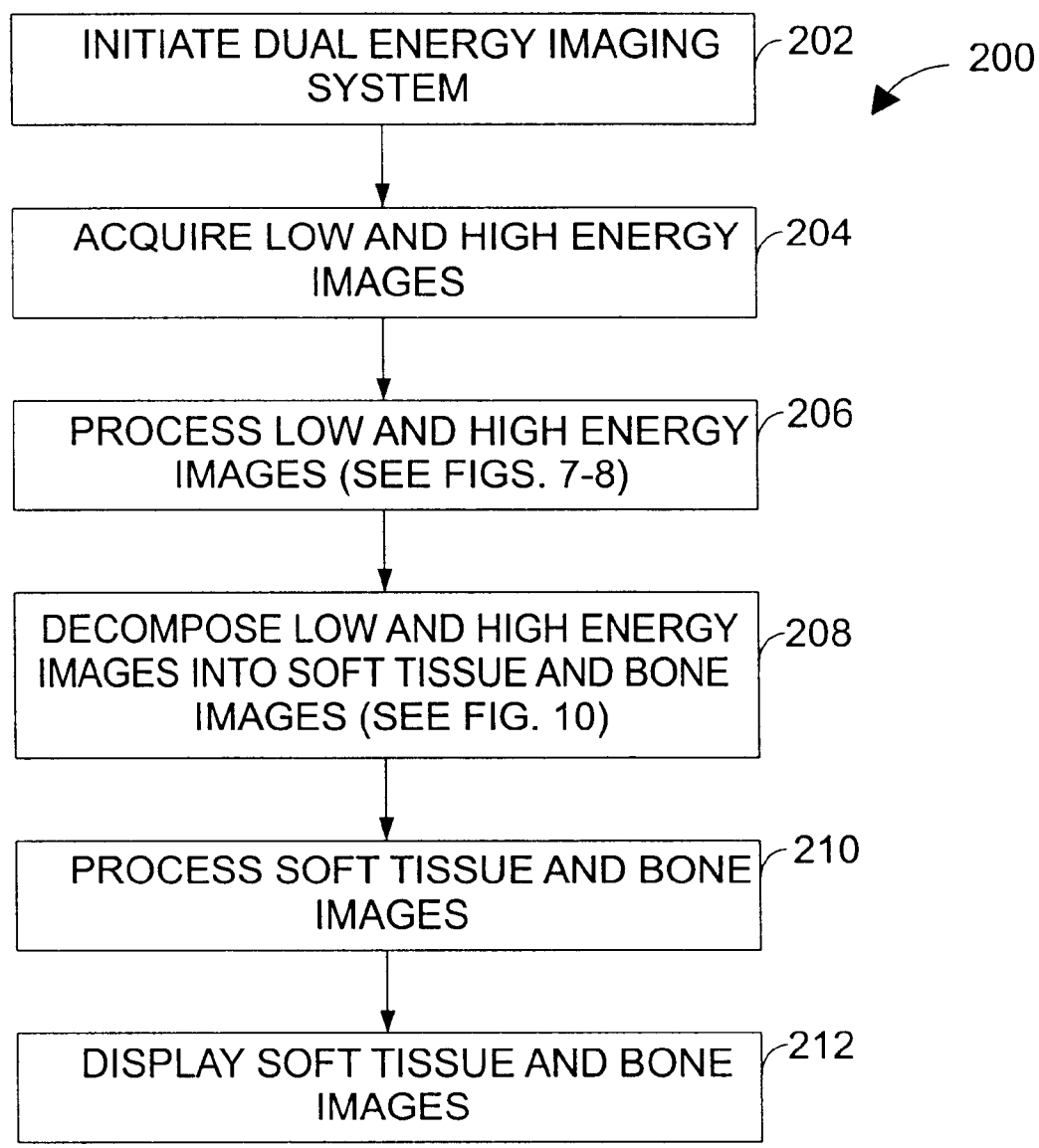
FIG. 6 is a flow chart illustrating an exemplary dual-energy image acquisition and processing scheme of the present technique.
Figure 7:
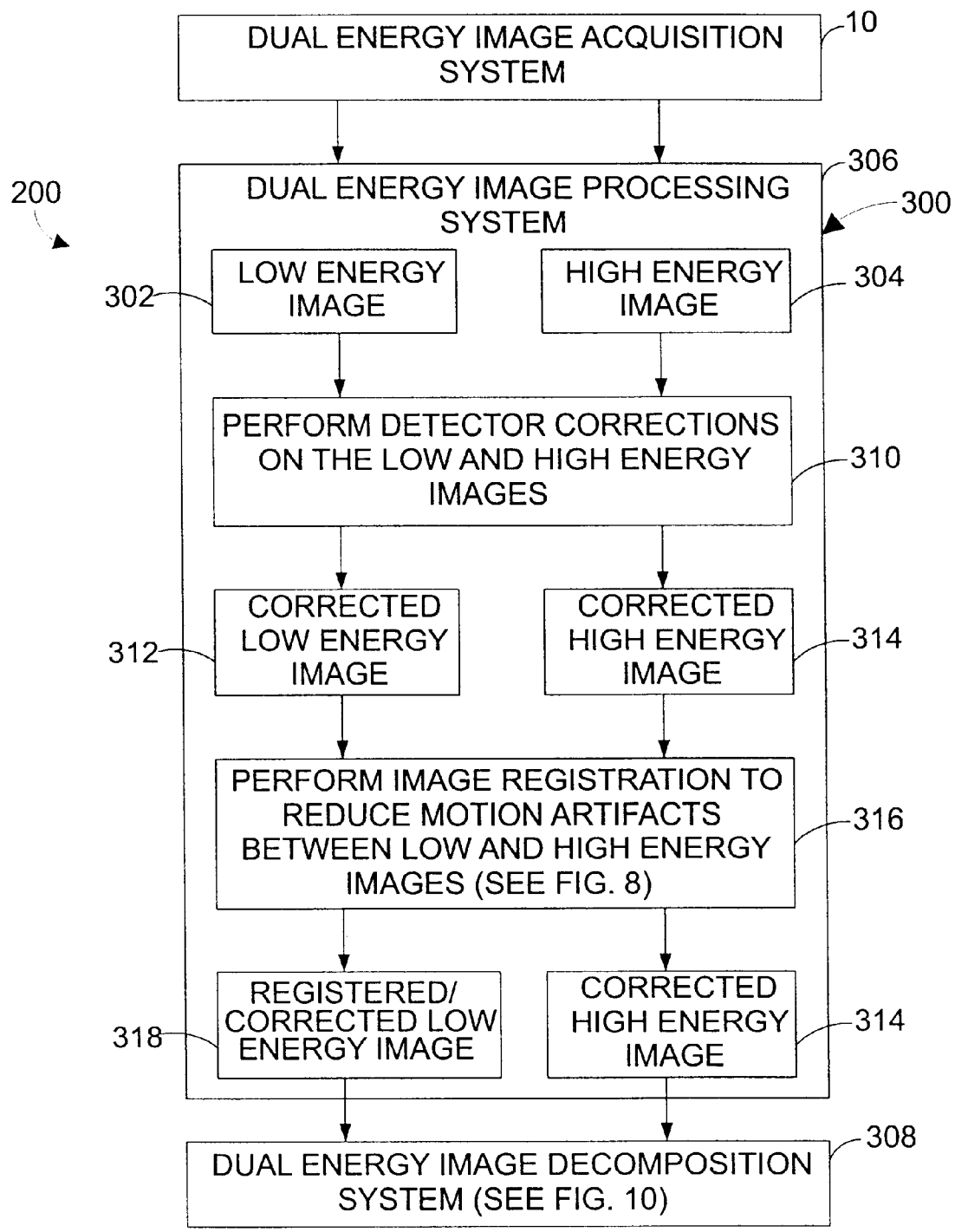
FIG. 7 is a flow chart illustrating an exemplary pre-decomposition processing scheme for the scheme of FIG. 6.

FIG. 7 is a flow chart illustrating an exemplary pre-decomposition processing scheme 300 for performing the act of processing low and high-energy images, as illustrated by step 206 of FIG. 6. As illustrated, the dual-energy images acquisition system 10 provides a low-energy image 302 and a high-energy image 304 to a dual-energy image processing system 306, which processes the images 302 and 304 and passes the processed images to a dual-energy image decomposition system 308. Accordingly, the dual-energy image processing system 306 may perform a variety of processing routines on the images 302 and 304 prior to decomposition into soft tissue and bone images. As illustrated, the system 306 performs detector corrections on the low and high-energy images (block 310). For example, the system 306 may correct the low and high-energy images 302 and 304 for variations in the x-ray imaging detectors to provide a corrected low-energy image 312 and a corrected high-energy image 314. The system 306 may then proceed to perform image registration on the corrected low and high-energy images 312 and 314 to reduce motion artifacts between the images, as further illustrated by FIG. 8 (block 316). Accordingly, the system 306 may register the corrected low-energy image 312 to the corrected high-energy image 314 by performing image transformations on either of the images 312 and 314. In this exemplary embodiment, the system 306 transforms the corrected low-energy image 312 to provide a registered low-energy image 318, which is registered (e.g., spatially matched) to the corrected high-energy image 314.

Figure 8:
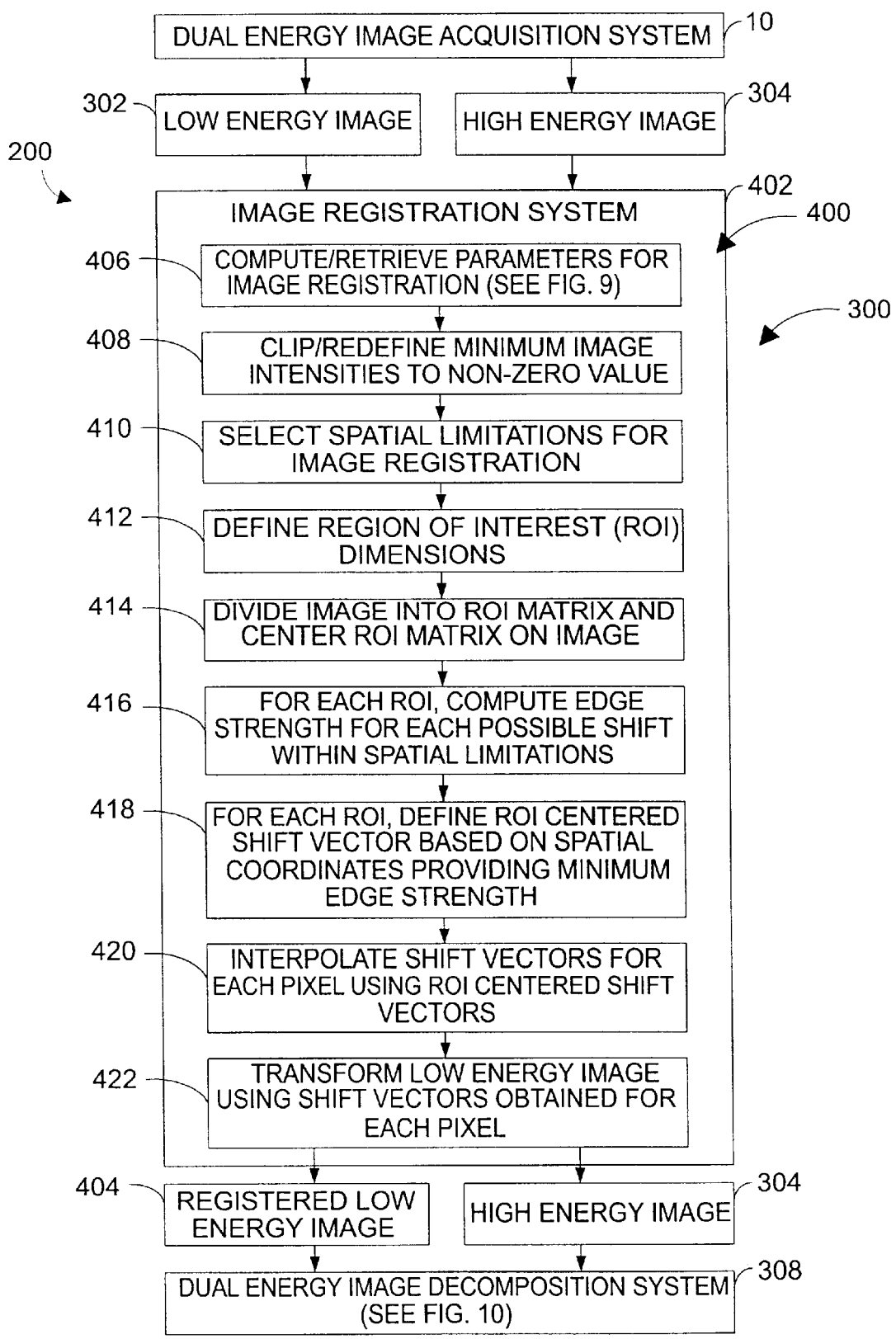
FIG. 8 is a flow chart illustrating an exemplary image registration process for the pre-decomposition processing scheme of FIG. 7.

FIG. 8 is a flow chart illustrating an exemplary image registration process 400 for the pre-decomposition processing scheme 300 of FIG. 7. An image registration system 402 performs the process 400 by executing a variety of image registration routines on the low and high-energy images 302 and 304, which are acquired by the dual-energy image acquisition system 10. Upon completion, the system 402 passes a registered low-energy image 404 and the high-energy image 304 to the dual-energy image decomposition system 308. As described in detail below, the process 400 registers the low and high-energy images 302 and 304 by obtaining shift vectors of one image with respect to the other. A warping transformation is then performed on the low-energy image 302 to align the anatomy with respect to the high-energy image 304 prior to dual-energy decomposition into soft tissue and bone images. The process 400 is computationally efficient because the motion artifacts are constrained to only a few pixels due to the relatively short time interval between the low and high-energy image exposures. The process 400 is also advantageously insensitive to the contrast differences between the low and high-energy images 302 and 304. Accordingly, the soft tissue and bone images subsequently produced by dual-energy decomposition exhibit significantly reduced motion artifacts.

Figure 9:
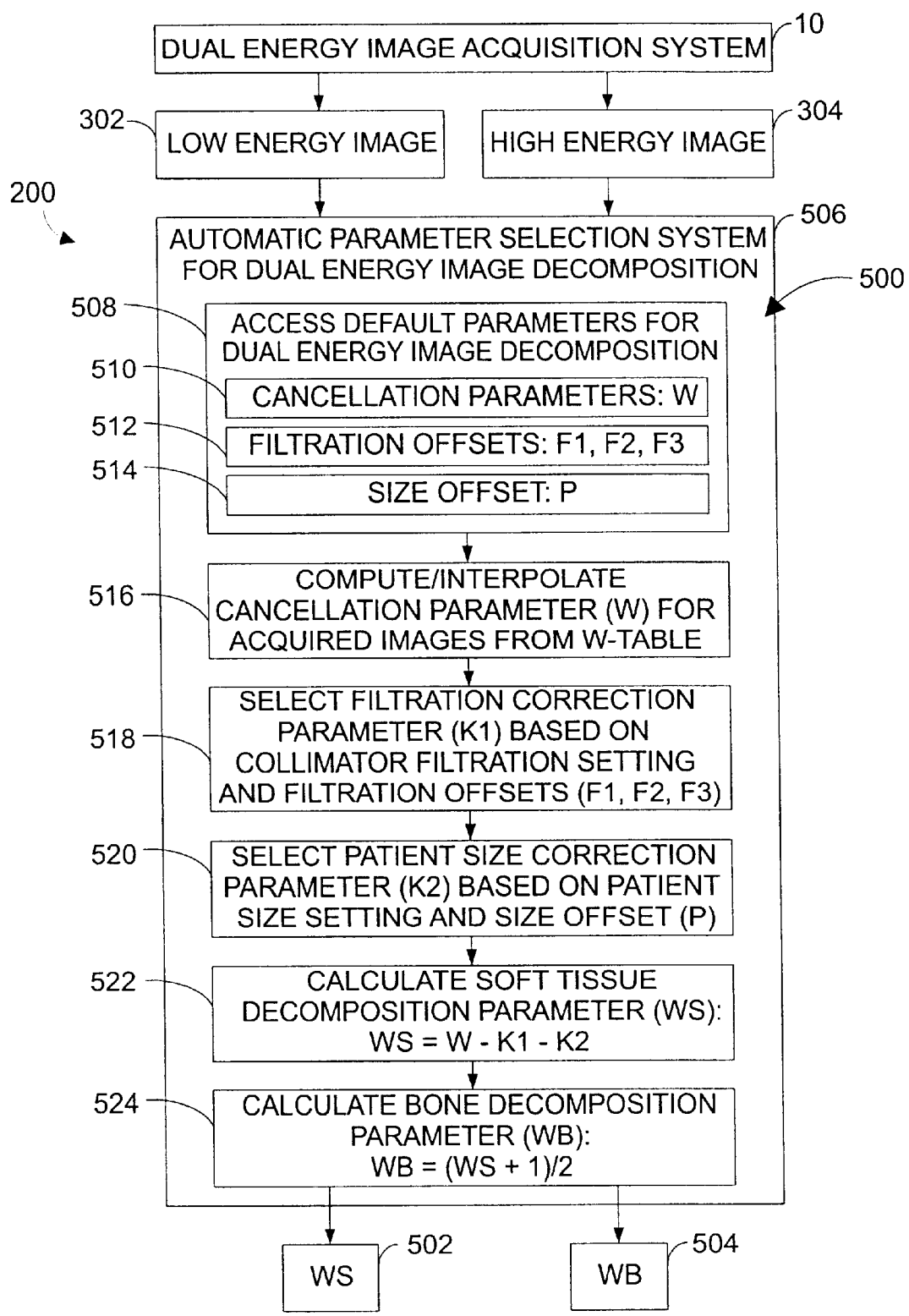
FIG. 9 is a flow chart illustrating an exemplary parameter selection process for dual-energy image decomposition processes, such as illustrated by FIGS. 6–8 and 10–12.

In operation, the system 402 proceeds by computing or retrieving a variety of image registration parameters, as further illustrated by FIG. 9 (block 406). The system 402 then proceeds to clip or redefine the minimum image intensities of the low and high-energy images 302 and 304 to nonzero values, such as a value of 1 (block 408). Step 408 prevents errors associated with division by zero. The system 402 then proceeds to select, or prompt the user to input, spatial limitations for image registration (block 410). For example, a search space (S) may be selected to control the degree of image warping/transformation by the image registration process 400. The search space S is an integer defining the maximum number of pixels that any point in the image being registered (i.e., the low-energy image 302) is allowed to shift in either the X or Y direction. For example, if S=3, then the search space is a seven pixel by seven pixel matrix centered on the point of interest. The system 402 then proceeds to define, or prompt the user to input, dimensions for a region of interest (ROI) for the image registration process 400 (block 412). For example, the region of interest ROI may be less than, equal to, or larger than the search space S. The system 402 then proceeds to divide the image (i.e., the low-energy image 302) into an ROI matrix comprising the maximum number of non-overlapping contiguous ROIs centered within the image and leaving a border to allow for image shifting (block 414). The pixels outside the ROI matrix are border pixels, which may be equal to or greater than the search range (e.g., S=3). The system 402 then performs various computations on the low and high-energy images 302 and 304.

For each ROI, the system 402 computes an edge strength for each possible shift within the spatial limitations defined by the search space S (block 416). Accordingly, for each ROI of the low-energy image 302 (IL), the system 402 shifts the ROI center to each possible location in the search space S. Each shifted ROI defines a low-energy sub-image (IL'$_{X,Y}$), where X and Y are the shift vector components in horizontal and vertical pixels, respectively. The unshifted ROI also defines a corresponding high-energy sub image (IH'$_{0,0}$). Accordingly, for each possible shift of the ROI in the search space S, the system 402 derives a pseudo-soft-tissue sub-image (I$_{PST}$)'$_{X,Y}$ by performing the log-subtraction operation:

$$(I_{PST})'_{X,Y} = (IH'_{0,0})/(IL'_{X,Y})^{WS}$$

where WS is a soft tissue decomposition parameter that may be selected as illustrated by FIG. 9. The system 402 then proceeds to obtain an edge sub-image (I$_E$)'$_{X,Y}$ by convolving (I$_{PST}$)'$_{X,Y}$ with a Prewit edge operator (e.g., two 3×3 kernels). This operation may leave a border, such as a 1 pixel border, on the resulting image. The system 402 then obtains a total edge strength E$_{X,Y}$ by summing all values in the edge sub-image (I$_E$)'$_{X,Y}$, excluding the foregoing 1 pixel border. The foregoing computations are repeated for each possible shift of the ROI in the search space S.

For each ROI, the system 402 then proceeds to determine the shift vector for registering the low-energy image 302 to the high-energy image 304. Accordingly, for each ROI, the system 402 defines the ROI-centered shift vector based on the (X,Y) spatial coordinates that minimize the total edge strength E$_{X,Y}$ computed above (block 418). The system 402 then uses the ROI-centered shift vectors to interpolate shift vectors for each pixel in the low-energy image 302 (block 420). For example, bilinear interpolation may be used to compute the shift vectors for each pixel in the low-energy image 302. The individual pixel shift vectors may then be rounded to integer values. In the border area surrounding the ROI matrix, the individual pixel shift vectors may be computed by replicating the shift vectors from the closest point, or from several adjacent points, within the ROI matrix.

Accordingly, the edge-based technique of the process 400 obtains shift vectors that minimize motion artifacts. The system 402 may then proceed to transform the low-energy image 302 using the individual pixel shift vectors computed above (block 422). Accordingly, the system 402 transforms or warps the low-energy image (IL) to form the registered low-energy image 404 (IL$_R$), which is registered to the high-energy image 304. These images 404 and 304 are then passed to the dual-energy image decomposition system 308 for decomposition into soft tissue and bone images.

As mentioned above, FIG. 9 is a flow chart illustrating an exemplary parameter selection process 500 for dual-energy image decomposition processes, such as illustrated by FIGS. 6–8 and 10–12. The parameter selection process 500 uses a variety of system parameters of the dual-energy image acquisition system 10 and the patient to select soft tissue and bone decomposition parameters WS and WB, as indicated by reference numerals 502 and 504, respectively. In this exemplary embodiment, the process 500 selects the parameters 502 and 504 automatically without any direct user intervention. However, the process 500 may operate with some degree of user interaction and input depending on the particular application. An automatic parameter selection system 506 performs the process 500 by accessing low and high-energy images 302 and 304 acquired from system 10, system settings, patient information, and other information to facilitate an optimal selection of the parameters 502 and 504, which are required by the dual-energy image decomposition system 308.

The system 506 may be used to select parameters for any dual-energy decomposition process. For dual imaging of chest anatomy, the parameters 502 and 504 are determined primarily by the energy levels (kVp) of the low and high-energy images 302 and 304, the collimator filtration selection, and the patient size. Accordingly, the process 500 is tailored to these parameters for automatic selection of the parameters 502 and 504 for dual-energy image decomposition of chest anatomy. As illustrated, the process 500 proceeds by accessing a variety of parameters for dual-energy image decomposition, such as by reading default parameters from the system configuration file (block 508). For example, the process 500 may access default cancellation parameters (W), filtration offsets (F1, F2, F3), and size offsets (P), as indicated by reference numerals 510, 512, and 514, respectively. The process 500 also may prompt the user to input desired parameters to facilitate the selection/computation of decomposition parameters. The foregoing filtration offsets 512 correspond to the collimator filtration selection, while the size offsets 514 corresponds to the patient size selection. The process 500 also may restrict the parameter selection to low and high-energy images 302 and 304 having determined energy ranges, such as 60–80 kVp for the low-energy image 302 and 110–150 kVp for the high-energy image 304. If the energy levels of the low and high energy images 302 and 304 exceed these predetermined ranges, then the process 500 may generate an error message and terminate the automatic parameter selection process. Accordingly, the default cancellation parameter W may be retrieved from a W-table, such as illustrated below, which provides the cancellation parameter W for energy levels of the low and high-energy images 302 and 304 within the foregoing energy ranges.

| W-TABLE | | | | | |
|---|---|---|---|---|---|
| Energy Levels of High- | Energy Levels of Low-Energy Image in kVp | | | | |
| Energy Image in kVp | 60 | 65 | 70 | 75 | 80 |
| 150 | .37 | .41 | .46 | .50 | .55 |
| 140 | .39 | .44 | .49 | .54 | .59 |
| 130 | .41 | .46 | .51 | .56 | .62 |
| 120 | .44 | .49 | .54 | .59 | .65 |
| 110 | .47 | .52 | .58 | .64 | .71 |

If the low or high-energy levels of images 302 and 304 are between the energy values within the W-table, then the process 500 interpolates (e.g., bilinear interpolation) the cancellation parameter W from the W-table based on the actual energy levels of images 302 and 304 (block 516). The process 500 may then truncate the computed cancellation parameter W to a desired number of decimal places, such as two decimal places.

The default cancellation parameter W is then corrected by a variety of correction factors, such as filtration correction parameter K1 and a patient size correction parameter K2. As illustrated, process 500 selects the filtration correction parameter K1 based on collimator filtration settings and filtration offsets 512 (block 518). For example, the process 500 may select the filtration correction parameter K1 as follows:

| Collimator Filtration Setting | Set filtration correction parameter K1 to: |
|---|---|
| 0.0 mm Cu | K1 = 0 |
| 0.1 mm Cu | K1 = F1 |

-continued

| Collimator Filtration Setting | Set filtration correction parameter K1 to: |
|---|---|
| 0.2 mm Cu | K1 = F2 |
| 0.3 mm Cu | K1 = F3 |

The process 500 may use any suitable filtration settings, any number of filtration offsets, or fractions of the filtration offsets to facilitate the selection of an optimal filtration correction parameter K1. The process 500 also may provide different parameters depending on the specific imaging system 10 or the process 500 may set K1=0 for a particular imaging system 10.

The process 500 also defines the patient size correction parameter K2 based on the size of the patient diagnosed by the imaging system 10 (block 520). For example, the process 500 may define the patient size correction parameter K2 as follows:

| Patient Size | Set patient size correction parameter K2 to: |
|---|---|
| Small patient | K2 = −P |
| Medium patient | K2 = 0 |
| Large patient | K2 = P |

The process 500 may use any suitable size ranges (e.g., weight or dimensions) to define the patient size correction parameter K2. Moreover, the process 500 may use multiple size offsets P or fractions of the size offsets P to provide further patient size ranges, which may facilitate the selection of an optimal patient size correction factor.

Using the foregoing correction parameters K1 and K2, the process 500 proceeds to calculate corrected soft tissue and bone decomposition parameters WS and WB, respectively. At block 522, the process 500 calculates a soft tissue decomposition parameter WS as follows:

$$WS=W-K1-K2$$

At block 524, the process 500 calculates a bone decomposition parameter WB as follows:

$$WB=(WS+1)/2$$

As mentioned above, the process 500 may compute these decomposition parameters WS and WB automatically without any direct user intervention. Moreover, the process 500 avoids robustness problems associated with image-based algorithms, opting instead to compute the decomposition parameters WS and WB based on system and patient variables. Although the process 500 specifically correlates WS and WB to filtration and patient size parameters, the present technique may use any suitable system settings and patient data to compute optimal decomposition parameters for the decomposition of a desired anatomy.

Figure 10:
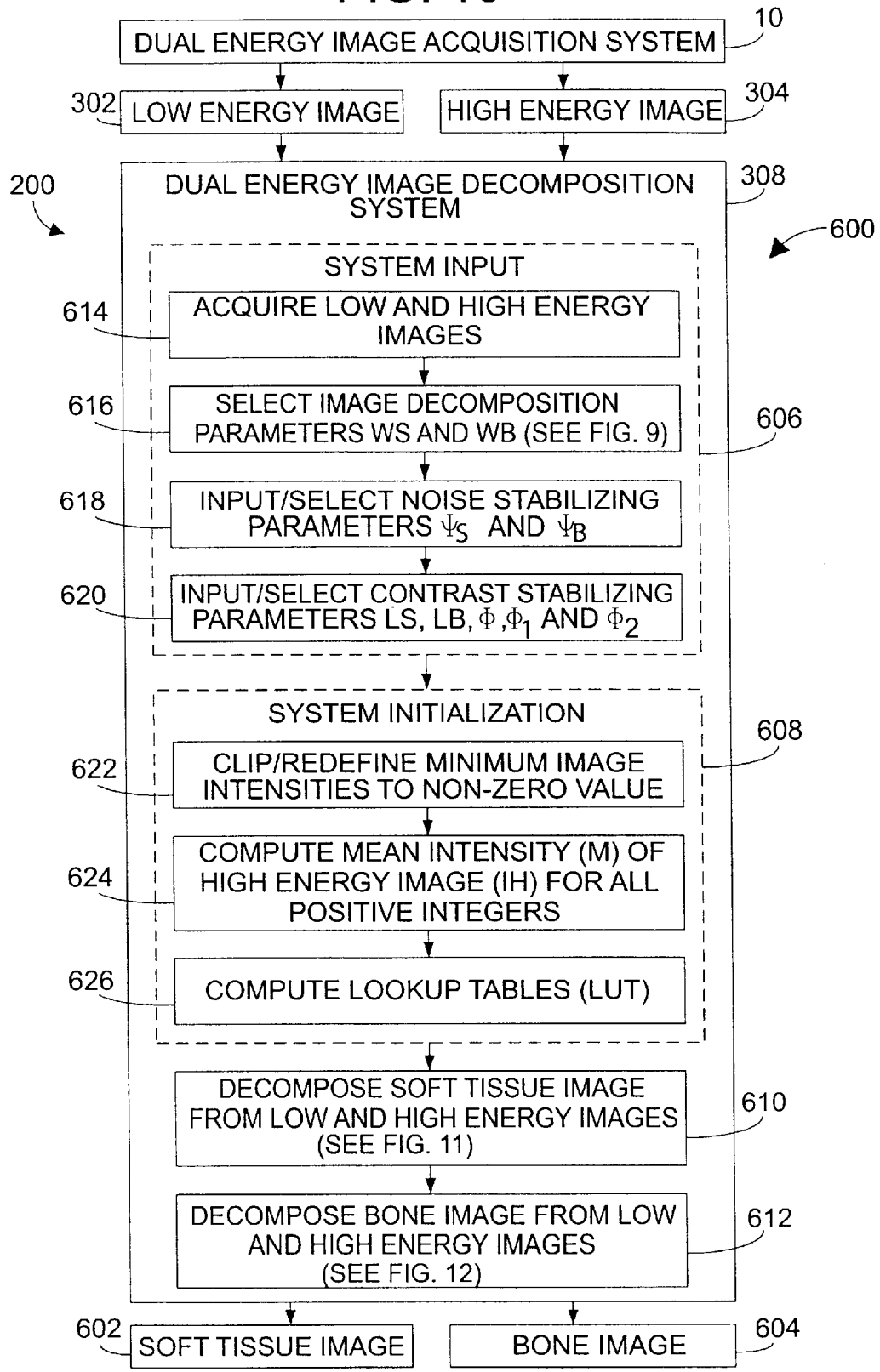
FIG. 10 is a flow chart illustrating an exemplary dual-energy image decomposition process for the scheme of FIG. 6.

FIG. 10 is a flow chart illustrating an exemplary dual-energy image decomposition process 600 for performing the act of decomposing low and high-energy images 302 and 304 into soft tissue and bone images 602 and 604, as illustrated by step 208 of FIG. 6. As illustrated, the dual-energy images acquisition system 10 provides the low-energy image 302 and the high-energy image 304 to the dual-energy image decomposition system 308, which executes a system input block 606, a system initialization block 608, and image decomposition blocks 610 and 612 to generate the soft tissue and bone images 602 and 604. As described in detail below, the dual-energy image decomposition system 308 performs a variety of operations to reduce/stabilize noise and to stabilize contrast of the images 602 and 604 that are decomposed from the low and high-energy images 302 and 304.

The soft tissue and bone images 302 and 304 are generally decomposed from the images 302 and 304 according to the dual-energy decomposition equations:

$$IS=IH/IL^{WS}$$

$$IB=IH/IL^{WB}$$

where IS represents the soft tissue image, IB represents the bone image, IH represents the high-energy image, IL represents the low-energy image, WS is the soft tissue decomposition parameter, WB is the bone decomposition parameter, and 0<WS<WB<1. However, this computationally efficient decomposition algorithm produces relatively noisy decomposed images at highly attenuated regions of the image during a low-dose clinical data acquisition. Accordingly, the system 308 uses a modified dual-energy decomposition scheme (e.g., process 600) to mitigate the noise amplification during the decomposition at highly attenuated regions and to provide a robust decomposition prior to further noise mitigation.

As illustrated, process 600 acquires or computes a variety of image data and parameters for the decomposition at the system input block 606. The system input block 606 begins by acquiring low and high-energy images 302 and 304 from the dual-energy image acquisition system 10 (block 614). For example, the system 308 may acquire rows and columns of image data for the low and high-energy images 302 and 304 from the dual-energy image acquisition system 10, which may embody digital flat-panel technology. The system input block 606 also selects/computes the image decomposition parameters WS and WB, such as illustrated by the automatic parameter selection process of FIG. 9 (block 616).

In this modified decomposition scheme, the system input block 606 also inputs a variety of image stabilizing parameters for use in modifying the dual-energy decomposition equations provided above. For example, the system input block 606 inputs/selects noise stabilizing parameters $\Psi_S$ and $\Psi_B$, which facilitate noise reduction/stabilization for the decomposition of the soft tissue and bone images 602 and 604, respectively (block 618). The foregoing stabilizing parameters may be obtained by experimentation with decomposition for the desired anatomy. For example, the stabilizing parameter $\Psi_S$ for reducing noise in the soft tissue image 602 may range from 1 to 5, but may have a preferred value of 1.4. The stabilizing parameter $\Psi_B$ for reducing noise in the bone image 604 also may range from 1 to 5. However, the value of $\Psi_B$ is a trade-off between noise and blooming artifacts in highly attenuated regions of the image. At $\Psi_B=1.0$, the modified decomposition scheme generates the bone image 604 with relatively no blooming artifacts, but with relatively significant noise. At $\Psi_B>1.0$, the modified decomposition scheme generates the bone image 604 with increasingly more blooming artifacts, but with increasingly less noise. Accordingly, the stabilizing parameter $\Psi_B$ may have a preferred value of 3 to 4 to stabilize the image.

The system input block 606 also inputs/selects contrast stabilizing parameters LS, LB, Φ, $\Phi_1$, and $\Phi_2$, which facilitate contrast stabilization for the decomposition of the soft tissue and bone images 602 and 604, respectively (block 620). For example, the stabilizing parameter Φ for contrast matching may be computed from the decomposition parameters WS and WB, as follows:

$$\Phi = WB/(WB-WS)$$

The remaining stabilizing parameters may be obtained by experimentation with decomposition for the desired anatomy. For example, the stabilizing parameter $\Phi_1$ for removing contrast abnormalities (e.g., irregular intensities) in the soft tissue image 602 may range from 1 to 100, but may have a preferred value of 10. Similarly, the stabilizing parameter $\Phi_2$ for removing contrast abnormalities (e.g., irregular intensities) in the bone image 604 may have a preferred value of 1.

The process 600 also performs a variety of initialization operations, such as illustrated by the system initialization block 608. As illustrated, the system initialization block 608 clips/redefines the minimum image intensities of the low and high-energy images 302 and 304 to be nonzero and positive values (block 622). For example, if a pixel intensity value is zero, then block 622 may redefine the pixel intensity value to a positive integer value of 1. The foregoing operation prevents division by 0 in the dual-energy decomposition equations. The system initialization block 608 also computes the mean intensity (M) of the high-energy image (IH) 304 for all nonzero positive values (block 624). The mean intensity (M) is used by the modified decomposition scheme to renormalize the decomposed bone image 604 following noise and contrast stabilization. The system initialization block 608 also computes lookup tables (LUTS) for $IL^{WS}$ and $IL^{WB}$, which are used in the modified dual-energy decomposition scheme (block 626). The lookup tables (LUTs) are computed only for the known intensity range of the dual-energy image acquisition system 10 or the image 302 (e.g., intensities of a 2k×2k pixel image). For example, the system 10 may have an intensity range comprising integer values of 0 to 16383. The lookup tables (LUTs) are subsequently used by the modified dual-energy decomposition scheme to perform the various decomposition and stabilization operations more efficiently.

Figure 11:
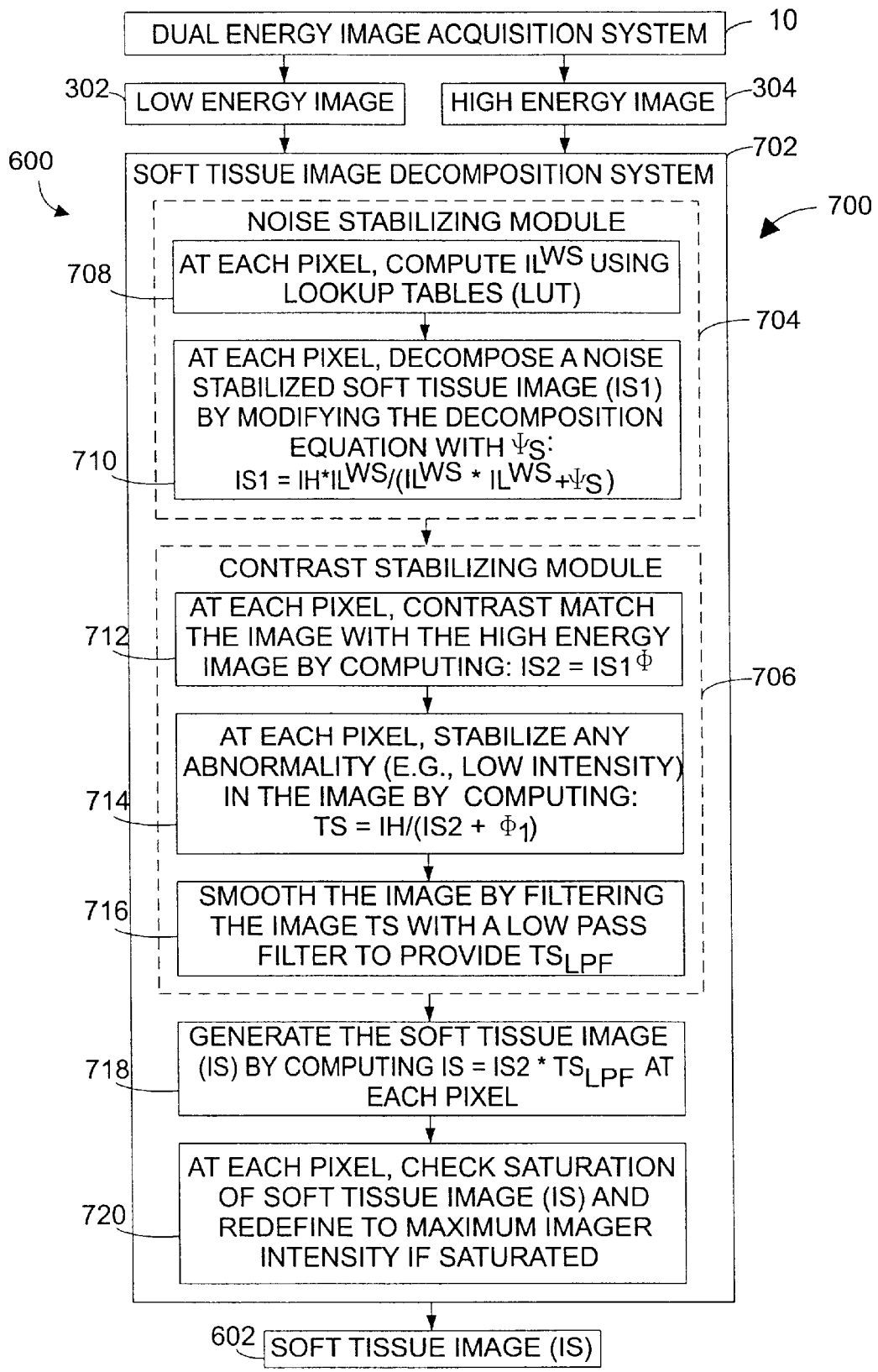
FIG. 11 is a flow chart illustrating an exemplary soft tissue image decomposition process for the scheme of FIG. 6.
Figure 12:
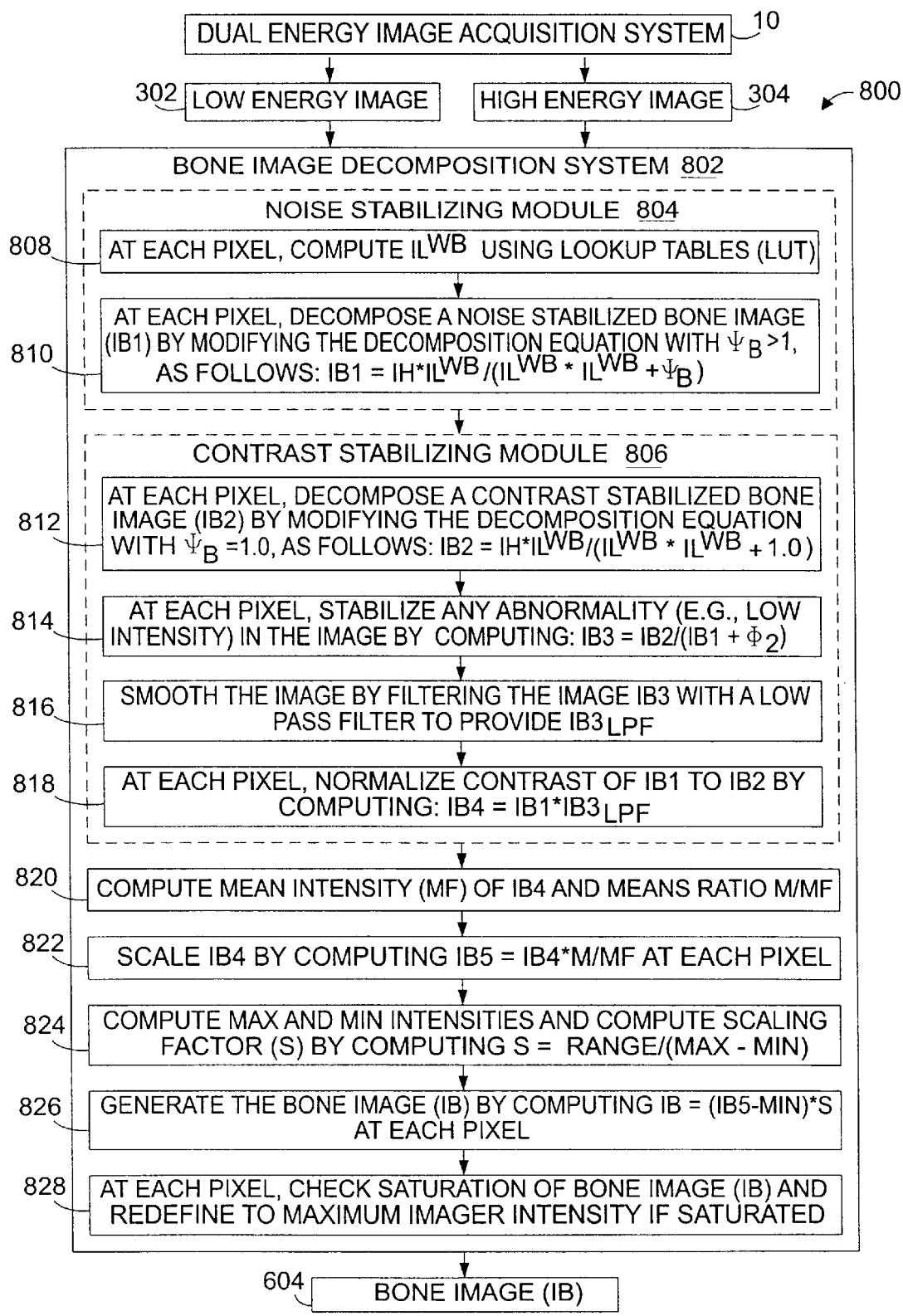
FIG. 12 is a flow chart illustrating an exemplary bone image decomposition process for the scheme of FIG. 6.

Accordingly, the process 600 uses the foregoing data and parameters input by block 606 and initialized by block 608 to decompose the soft tissue image 602 from the low and high-energy images 302 and 304, as illustrated by FIG. 11. The process 600 also uses the foregoing data and parameters to decompose the bone image 604 from the low and high-energy images 302 and 304, as illustrated by FIG. 12.

FIG. 11 is a flow chart illustrating an exemplary soft tissue image decomposition process 700 for performing the act of decomposing the soft tissue image 602 from the low and high-energy images 302 and 304, as illustrated by step 610 of FIG. 6. As illustrated, the soft tissue image decomposition process 700 is executed by a soft tissue image decomposition system 702, which comprises a noise stabilizing module 704 and a contrast stabilizing module 706 adapted to reduce/stabilize noise and to stabilize contrast during the decomposition of the soft tissue image 602 from the images 302 and 304. The soft tissue image decomposition process 700 is particularly advantageous for improving image quality at highly attenuated regions of the image caused by a low-dose clinical data acquisition.

As illustrated, the noise-stabilizing module 704 utilizes a modified decomposition equation:

$$IS1 = IH * IL^{WS}/(IL^{WS} * IL^{WS} + \Psi_S)$$

where IS1 is a noise reduced/stabilized soft tissue image, IL is the low-energy image 302, IH is the high-energy image 304, WS is the soft tissue decomposition parameter, and $\Psi_S$ is the soft tissue noise stabilizing parameter. The modified decomposition equation is equal to the general dual-energy decomposition equation only if $\Psi_S = 0$. However, at nonzero values of $\Psi_S$ (preferably $\Psi_S > 1$), the modified decomposition equation provides a robust decomposition that advantageously stabilizes noise at low values of $IL^{WS}$.

At each pixel, the stabilizing module 704 uses the lookup tables (LUTs) to compute $IL^{WS}$ for the foregoing modified decomposition equation (block 708). The stabilizing module 704 then proceeds pixel-by-pixel to compute the noise stabilized soft tissue image IS1 at the desired value for the noise stabilizing parameter $\Psi_S$ (block 710). As mentioned above, values of $\Psi_S > 1$ (e.g., $\Psi_S = 1$ to 5) mitigate the noise of the conventional dual-energy decomposition equation. However, a relatively high value of $\Psi_S$ defeats the purpose of decomposition, because high values of $\Psi_S$ produce an image that resembles the high-energy image 304. Accordingly, a value of $\Psi_S$ (e.g., $\Psi_S = 1.4$) may be selected to optimize the noise stabilization.

The process 700 then proceeds to stabilize the contrast via the contrast-stabilizing module 706. At block 712, the contrast-stabilizing module 706 proceeds pixel-by-pixel to contrast match the image with the high-energy image 304 by computing:

$$IS2 = IS1^{\Phi}$$

At block 714, the contrast stabilizing module 706 proceeds pixel-by-pixel to stabilize any abnormality, such as a low intensity pixel, in the image by computing:

$$TS = IH/(IS2 + \Phi_1)$$

As discussed above, $\Phi_1$ may range from 1 to 100, but preferably has a value of 10. The stabilizing parameter $\Phi_1$ corrects image abnormalities (e.g., a low pixel intensity) by adding $\Phi_1$, thereby returning the particular pixel to a relatively normal intensity range.

The contrast stabilizing module 706 then proceeds to block 716, where the image is smoothed by filtering the image data TS with a low pass filter to provide a filtered image $TS_{LPF}$. For example, the image data TS may be filtered using a standard boxcar filter, which smoothes the image by the average of a given neighborhood using a separable and efficient computation. Each point in the image requires just four arithmetic operations, irrespective of the kernel size LS, which controls the amount of smoothing. The length of the separable kernel is variable, but a preferred value of LS=151 may be used for a 2048×2048 image. Accordingly, the foregoing blocks 712 through 716 of the contrast-stabilizing module 706 operate to stabilize the contrast of the decomposed and noise-stabilized soft tissue image IS1.

At block 718, the process 700 proceeds pixel-by-pixel to generate the soft tissue image (IS) by computing:

$$IS = IS2 * TS_{LPF}$$

The process 700 also performs a saturation check at each pixel of the soft tissue image (block 720). A particular pixel is saturated if it exhibits an intensity equal to the maximum possible intensity (i.e., RANGE) of the imaging system 10. For example, if the low-energy image (IL) 302 and the high-energy image (IH) 304 both exhibit intensities equal to the maximum possible intensity (RANGE) of the imaging system 10, then the process 700 may redefine the image IS to equal the maximum intensity at that particular pixel (i.e., IS=RANGE).

The soft tissue image generated by the foregoing process 700 exhibits relatively lower noise and relatively more stabilized contrast than a soft tissue image decomposed by the conventional dual-energy decomposition equation. As mentioned above, the stabilizing parameters may be selected to optimize the image quality for a particular imaging system and anatomy (e.g., chest radiography). Accordingly, the process 700 may produce noise and contrast-stabilized soft tissue images for any application by identifying the optimal stabilizing parameters experimentally or empirically.

FIG. 12 is a flow chart illustrating an exemplary bone image decomposition process 800 for performing the act of decomposing the bone image 604 from the low and high-energy images 302 and 304, as illustrated by step 612 of FIG. 6. As illustrated, the bone image decomposition process 800 is executed by a bone image decomposition system 802, which comprises a noise stabilizing module 804 and a contrast stabilizing module 806 adapted to reduce/stabilize noise and to stabilize contrast during the decomposition of the bone image 604 from the images 302 and 304. The bone image decomposition process 800 is particularly advantageous for improving image quality at highly attenuated regions of the image caused by a low-dose clinical data acquisition.

As illustrated, the noise-stabilizing module 804 utilizes a modified decomposition equation:

$$IB1=IH*IL^{WB}/(IL^{WB}*IL^{WB}+\Psi_B)$$

where IB1 is a noise reduced/stabilized bone image, IL is the low-energy image 302, IH is the high-energy image 304, WB is the bone decomposition parameter, and $\Psi_B$ is the bone noise stabilizing parameter. The modified decomposition equation is equal to the general dual-energy decomposition equation only if $\Psi_B=0$. However, at nonzero values of $\Psi_B$ (preferably $\Psi_B>1$), the modified decomposition equation provides a robust decomposition that advantageously stabilizes noise at low values of $IL^{WB}$.

At each pixel, the stabilizing module 804 uses the lookup tables (LUTs) to compute $IL^{WB}$ for the foregoing modified decomposition equation (block 808). The stabilizing module 804 then proceeds pixel-by-pixel to compute the noise-stabilized bone image IB1 at the desired value for the noise stabilizing parameter $\Psi_B$ (block 810). As mentioned above, values of $\Psi_B>1$ (e.g., $\Psi_B=1$ to 5) mitigate the noise of the conventional dual-energy decomposition equation. However, a relatively high value of $\Psi_B$ defeats the purpose of decomposition, because high values of $\Psi_B$ produce an image that resembles the high-energy image 304. Accordingly, a value of $\Psi_B$ (e.g., $\Psi_B=3$ or 4) may be selected to optimize the noise stabilization.

The process 800 then proceeds to stabilize the contrast via the contrast-stabilizing module 806. As discussed above, the value of $\Psi_B$ is a trade-off between noise and blooming artifacts in highly attenuated regions of the image. At $\Psi_B>1.0$, the modified decomposition scheme generates the bone image 604 with increasingly more blooming artifacts, but with increasingly less noise. The image IB1 computed at block 812 captures this low noise phenomenon. At $\Psi_B=1.0$, the modified decomposition scheme generates the bone image 604 with relatively no blooming artifacts, but with relatively significant noise. The process 800 captures this low/no blooming artifacts phenomenon at block 812, where the contrast stabilizing module 806 proceeds pixel-by-pixel to compute a contrast-stabilized bone image (IB2), as follows:

$$IB2=IH*IL^{WB}/(IL^{WB}*IL^{WB}+1.0)$$

At block 814, the contrast-stabilizing module 806 proceeds pixel-by-pixel to stabilize any abnormality, such as a low intensity pixel, in the image by computing:

$$IB3=IB2/(IB1+\Phi_2)$$

As discussed above, $\Phi_2$ may range from 1 to 100, but preferably has a value of 1.0. The stabilizing parameter $\Phi_2$ corrects image abnormalities (e.g., a low pixel intensity) by adding $\Phi_2$, thereby returning the particular pixel to a relatively normal intensity range.

The contrast-stabilizing module 806 then proceeds to block 816, where the image is smoothed by filtering the image data IB3 with a low pass filter to provide a filtered image $IB3_{LPF}$. For example, the image data IB3 may be filtered using a standard boxcar filter, which smoothes the image by the average of a given neighborhood using a separable and efficient computation. Each point in the image requires just four arithmetic operations, irrespective of the kernel size LB, which controls the amount of smoothing. The length of the separable kernel is variable, but a preferred value of LB=151 may be used for a 2048×2048 image.

At block 818, the contrast-stabilizing module 806 combines the low noise properties of the decomposed image IB1 with the low/no blooming artifacts properties of the decomposed image IB2 by computing:

$$IB4=IB1*IB3_{LPF}$$

The contrast matching operation of block 818 normalizes the contrast of IB1 to IB2, thereby allowing use of higher values of $\Psi_B$ in the modified decomposition equation to provide improved noise mitigation without producing blooming artifacts. In comparison to the modified decomposition of soft tissue images, the bone image decomposition process 800 generally requires a higher value of the stabilizing parameter $\Psi_B$ due to relatively higher noise in the bone images. Accordingly, the internal matching of the noise stabilized and contrast stabilized bone images provide an exceptional bone image for analysis by the physician.

The foregoing blocks of process 800 produce a fractional decomposed bone image, which necessitates a scaling operation to return decomposed bone image back to the original intensity levels. Accordingly, at block 820, the process 800 proceeds to compute the mean intensity (MF) of the image data IB4 and a ratio of means M/MF, where M is the mean intensity of the high-energy image 302 for all nonzero positive values. At block 822, the process 800 proceeds pixel-by-pixel to scale the bone image data IB4 with the ratio of means, as follows:

$$IB5=IB4*M/MF$$

The process 800 then computes the maximum (MIN) and minimum (MAX) intensities of the image data IB5 by averaging 2×2 neighborhoods of the image data IB5 (block 824). The process 800 also computes a scaling factor (S) at block 824, by computing:

$$S=RANGE/(MAX-MIN)$$

where RANGE is the intensity range of the image acquisition system 10.

At block 826, the process 800 proceeds pixel-by-pixel to generate the bone image (IB) by scaling the image data IB5, as follows:

$$IB=(IB5-MIN)*S$$

The process 800 also performs a saturation check at each pixel of the bone image (block 828). A particular pixel is saturated if it exhibits an intensity equal to the maximum possible intensity (i.e., RANGE) of the imaging system 10. For example, if the low-energy image (IL) 302 and the high-energy image (IH) 304 both exhibit intensities equal to the maximum possible intensity (RANGE) of the imaging system 10, then the process 800 may redefine the image IB to equal the maximum intensity at that particular pixel (i.e., IB=RANGE).

The bone image generated by the foregoing process 800 exhibits relatively lower noise and relatively more stabilized contrast than a bone image decomposed by the conventional dual-energy decomposition equation. As mentioned above, the stabilizing parameters may be selected to optimize the image quality for a particular imaging system and anatomy (e.g., chest radiography). Accordingly, the process 800 may produce noise and contrast-stabilized bone images for any application by identifying the optimal stabilizing parameters experimentally or empirically.

The present technique also may comprise a system and process for interactively selecting or modifying one or more parameters associated with decomposing the soft tissue image 602 and the bone image 604 from the low-energy image 302 and high-energy image 304. This manual override or interactive modification technique is particularly advantageous for imaging systems that may drift out of calibration over time. For example, a user interface may allow the user to input or modify any of the foregoing decomposition parameters, including the soft tissue decomposition parameter WS, the bone decomposition parameter WB, the noise stabilizing parameters $\Psi_S$ and $\Psi_B$, the contrast stabilizing parameters LS, LB, $\Phi$, $\Phi_1$, and $\Phi_2$, or any other such parameters. FIG. 13 illustrates an exemplary post-decomposition processing scheme 900 for enhancing the decomposed soft tissue and bone images 602 and 604 and for modifying decomposition parameter data based on a modification of the soft tissue and bone images.

As illustrated, the dual energy image acquisition system 10 produces the low-energy image 302 and the high-energy image 304. The automatic parameter selection system 506 is then used to select optimal decomposition parameters 502 and 504, which are passed to the dual energy image decomposition system 308. Unfortunately, the decomposition parameters 502 and 504 are based on defaults, which may not provide optimally decomposed images 602 and 604 due to system calibration drifting or other factors. The decomposition system 308 then uses the soft tissue and bone decomposition parameters 502 and 504, and any other default or user input parameters, to decompose the soft tissue and bone images 602 and 604. The process 900 then proceeds to an evaluation of the soft tissue and bone images, which may be displayed via any suitable graphical display or monitor (block 902). If the images are acceptable to the user at block 904, then the process 900 proceeds to end at block 912. Otherwise, if the soft tissue and bone images are not acceptable at block 904, then the process 900 proceeds to modify the soft tissue and bone images by changing one or more decomposition parameters interactively (block 906).

For example, the user may modify the decomposition parameters 502 and 504 by inputting new values, by moving an interactive slider, or by any other user input mechanism. If the user modifies one or more decomposition parameters using an interactive mechanism, such as an interactive slider, then the process 900 may automatically decompose new soft tissue and bone images 602 and 604 based on the modified parameters. Accordingly, the process 900 provides the user with an interactive image enhancement mechanism, which is associated directly with the parameters used for decomposing the soft tissue and bone images 602 and 604.

After modifying the soft tissue and bone images via interactive modification of the decomposition parameters, the process 900 may provide the user with an option to accept the modified soft tissue and bone images (block 908).

Alternatively, the process 900 may provide a parameter update option that is operable at any time by the user. If the user accepts the modified soft tissue and bone images, then the process 900 proceeds to modify the default data/parameters associated with the decomposition parameters for subsequent soft tissue and bone decomposition (block 910). For example, the process 900 may recalculate or redefine default parameters, such as default parameters 508 and the noise and contrast stabilizing parameters, based on the modified parameters in block 906. In one exemplary embodiment, the user may interactively modify the soft tissue and bone decomposition parameters WS and WB to achieve the desired image quality. The process 900 may then perform a reverse operation of the parameter selection system 506, as illustrated and described with reference to FIG. 9. For example, the process 900 may calculate a new/modified default cancellation parameter table (i.e., W-table) 510, one or more new/modified filtration offsets 512, and one or more new/modified size offsets 514. Similarly, the process 900 can modify any other default decomposition parameters to facilitate accurate soft tissue and bone decomposition for future imaging.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of improving image clarity of soft tissue and bone images decomposable from first and second energy images acquired by a digital radiography imaging system at different times, comprising the act of registering the first energy image to the second energy image using warping registration prior to decomposing the first and second energy images into the soft tissue and bone images.

2. The method of claim 1, wherein the act of registering the first energy image to the second energy image comprises the act of spatially matching anatomical features in the first and second energy images.

3. The method of claim 2, wherein the act of spatially matching anatomical features comprises the act of warping the first energy image relative to the second energy image.

4. The method of claim 1, wherein the act of registering the first energy image to the second energy image comprises the act of substantially reducing motion variations between the first and second energy images.

5. The method of claim 1, wherein the act of registering the first energy image to the second energy image comprises the act of computing shift vectors for transforming the first energy image relative to the second energy image.

6. The method of claim 5, wherein the act of computing shift vectors comprises the act of computing a pixel shift vector for each pixel of the first energy image.

7. The method of claim 5, wherein the act of computing shift vectors comprises the act of computing an area shift vector for each spatial area of a spatial matrix for the first energy image.

8. The method of claim 7, wherein the act of computing the area shift vectors comprises the act of defining the spatial matrix as a maximum number of non-overlapping spatial areas centered on the first energy image and retaining a border to allow for a desired search range of image shifting.

9. The method of claim 7, wherein the act of computing the area shift vector comprises the act of decomposing a soft tissue sub-image from the first and second energy images for each shift vector of a plurality of possible shift vectors for each spatial area of the spatial matrix.

10. The method of claim 9, wherein the act of computing the area shift vector comprises the act of selecting one shift factor of the plurality of possible shift vectors for the spatial area that provides a minimum total edge strength for the spatial area.

11. The method of claim 9, wherein the act of selecting one of the plurality of possible shift vectors comprises the acts of:
   limiting the plurality of possible shift vectors to a spatial search range;
   computing a total edge strength for each of the plurality of possible shift vectors within the spatial search range; and
   identifying the shift vector corresponding to the minimum total edge strength.

12. The method of claim 7, wherein the act of computing shift vectors comprises the act of interpolating pixel shift vectors for each pixel of the first energy image from the area shift vectors of adjacent spatial areas of the spatial matrix.

13. The method of claim 1, comprising the act of acquiring the first and second energy images at different energy levels, which comprise low and high energy levels.

14. The method of claim 13, wherein the act of acquiring the first and second energy images comprises the act of acquiring the first and second energy images over a time interval.

15. The method of claim 13, wherein the act of acquiring the first and second energy images is performed using flat-panel detector technology of the digital radiography imaging system.

16. The method of claim 1, comprising the act of decomposing the soft tissue and bone images from the first and second energy images after being registered.

17. A method of reducing motion artifacts for two exposure dual energy radiography prior to decomposition of soft tissue and bone images, comprising:
   obtaining first and second energy images from a digital radiography imaging system over a time interval;
   defining a maximum pixel range that any point in the first energy image is allowed to shift relative to the second energy image;
   defining a spatial matrix for analyzing the first energy image;
   decomposing a sub-image from the first and second energy images for each shift vector of a plurality of possible shift vectors for each spatial area of the spatial matrix;
   computing a total edge strength for each possible shift vector within the maximum pixel range for each spatial area of the spatial matrix;
   defining an area shift vector for each spatial area to be the shift vector that minimizes the total edge strength for the spatial area;
   computing a pixel shift vector for each pixel within the first energy image by interpolation based on adjacent area shift vectors; and
   registering the first energy image to the second energy image by warping the first energy image pixel-by-pixel using the pixel shift vectors.

18. The method of claim 17, wherein the act of defining the spatial matrix comprises the acts of:
   centering a maximum number of non-overlapping spatial areas on the first energy image; and
   retaining a border around the spatial matrix to allow for the maximum pixel range.

19. The method of claim 17, wherein the act of registering the first energy image to the second energy image comprises the act of spatially matching anatomical features in the first and second energy images.

20. The method of claim 19, wherein the act of spatially matching anatomical features comprises the act of warping the first energy image relative to the second energy image.

21. The method of claim 19, wherein the act of registering the first energy image to the second energy image comprises the act of substantially reducing motion variations between the first and second energy images.

22. The method of claim 19, wherein the first and second energy images correspond to low-energy and high-energy image acquisition levels, respectively.

23. The method of claim 19, wherein the first and second energy images correspond to first and second acquisition times over the time interval.

24. The method of claim 19, wherein the first and second energy images are acquired from the digital radiography imaging system using flat-panel detector technology.

25. The method of claim 19, comprising the act of decomposing soft tissue and bone images from the first and second energy images after being registered.

26. A method of producing soft tissue and bone images of the desired anatomy of a patient, comprising the acts of:
   acquiring first and second images of the desired anatomy at different times using a digital radiography imaging system having flat-panel detector technology, wherein one image of the first and second images is acquired at a low-energy level and a remaining image of the first and second images is acquired at a high-energy level;
   registering the first image to the second image using warping registration; and
   decomposing soft tissue and bone images of the desired anatomy from the warpingly registered first and second images.

27. The method of claim 26, wherein the act of acquiring the first and second images of the desired anatomy comprises the act of imaging chest anatomy over a time interval.

28. The method of claim 26, wherein the act of registering the first image to the second image comprises the act of spatially matching anatomical features in the first and second images.

29. The method of claim 28, wherein the act of spatially matching anatomical features comprises the act of warping the first image relative to the second image.

30. The method of claim 26, wherein the act of registering the first image to the second image comprises the act of substantially reducing motion variations between the first and second images corresponding to movement of the desired anatomy during acquisition of the first and second images.

31. The method of claim 26, wherein the act of registering the first image to the second image comprises the act of computing shift vectors for transforming the first image relative to the second image.

32. The method of claim 31, wherein the act of computing shift vectors comprises the act of computing a pixel shift vector for each pixel of the first image.

33. The method of claim 31, wherein the act of computing shift vectors comprises the act of computing an area shift vector for each spatial area of a spatial matrix for the first image.

34. The method of claim 33, wherein the act of computing the area shift vectors comprises the act of defining the spatial matrix as a maximum number of non-overlapping spatial areas centered on the first image and retaining a border to allow for a desired search range for pixel shifting.

35. The method of claim 33, wherein the act of computing the area shift vector comprises the acts of:
  decomposing a sub-image from the first and second images for each shift vector of a plurality of possible shift vectors for each spatial area of the spatial matrix; and
  selecting one shift vector of the plurality of possible shift vectors for the spatial area that provides a minimum total edge strength for the spatial area.

36. The method of claim 35, wherein the act of selecting one of the plurality of possible shift vectors comprises the acts of:
  limiting the plurality of possible shift vectors to a spatial search range;
  computing a total edge strength for each of the plurality of possible shift vectors within the spatial search range; and
  identifying the shift vector corresponding to the minimum total edge strength for the spatial area.

37. The method of claim 33, wherein the act of computing shift vectors comprises the act of interpolating pixel shift vectors for each pixel of the first image from the area shift vectors of adjacent spatial areas of the spatial matrix.

38. A computer program for processing image data acquired from a digital radiography imaging system, comprising:
  a tangible medium configured to support machine-readable code; and
  machine-readable code supported on the medium and comprising a pre-decomposition warping-image-registration routine adapted to register first and second images prior to decomposition into soft tissue and bone images, wherein the first and second images are obtained from the digital radiography imaging system at different energy levels and different times.

39. The computer program of claim 38, wherein the machine-readable code comprises an acquisition routine adapted to acquire the first and second images at the different energy levels, which comprise low and high energy levels.

40. The computer program of claim 39, wherein the acquisition routine comprises a timing routine adapted to acquire the first and second images over a time interval.

41. The computer program of claim 38, wherein the machine-readable code comprises a decomposition routine adapted to decompose the soft tissue and bone images from the first and second images after being registered.

42. The computer program of claim 38, wherein the pre-decomposition image registration routine comprises a routine for spatially matching anatomical features in the first and second images.

43. The computer program of claim 42, wherein the routine for spatially matching anatomical features is adapted to reduce motion variations between the first and second images.

44. The computer program of claim 38, wherein the pre-decomposition image registration routine comprises a routine adapted to compute shift vectors to warp the first image relative to the second image.

45. The computer program of claim 44, wherein the routine for computing shift vectors comprises a routine adapted to compute a pixel shift vector for each pixel of the first image.

46. The computer program of claim 44, wherein the routine for computing shift vectors comprises a routine adapted to compute an area shift vector for each spatial area of a spatial matrix for the first image.

47. The computer program of claim 46, wherein the routine adapted to compute the area shift vector comprises:
  a sub-image decomposition routine adapted to decompose a soft tissue sub-image from the first and second images for each shift vector of a plurality of possible shift vectors for each spatial area of the spatial matrix; and
  a selection routine adapted to select one shift vector of the plurality of possible shift vectors in a maximum shift search range for the spatial area that provides a minimum total edge strength for the spatial area.

48. The computer program of claim 46, wherein the routine adapted to compute shift vectors comprises an interpolation routine adapted to interpolate pixel shift vectors for each pixel of the first image from the area shift vectors of adjacent spatial areas of the spatial matrix.

49. A medical imaging system, comprising:
  a digital radiographic imaging system, comprising:
    an x-ray device adapted to generate x-rays;
    a collimator adapted to filter the x-rays in a desired anatomical region of a patient;
    a flat-panel digital x-ray detector adapted to detect x-rays passing through the patient; and
    dual-energy control circuitry adapted to acquire first and second images of the desired anatomical region at different energy levels over a time interval; and
  an image processing system, comprising:
    a pre-decomposition processing module adapted to register the first image to the second image using warping registration prior to decomposition; and
    a dual-energy image decomposition module adapted to decompose soft tissue and bone images from the warpingly registered first and second images.

50. The medical imaging system of claim 49, wherein the pre-decomposition processing module comprises machine-readable code for spatially matching anatomical features in the first and second images.

51. The medical imaging system of claim 50, wherein the machine-readable code comprises an image warping routine operable to reduce motion variations between the first and second images.

52. The medical imaging system of claim 51, wherein the image warping routine comprises an edge-strength-based routine adapted to compute shift vectors to warp areas of the first image relative to the second image.

53. The medical imaging system of claim 52, wherein the edge-strength-based routine comprises a region of interest analysis routine adapted to decompose a sub-image from the first and second images for each shift vector of a plurality of possible shift vectors for each area of a spatial matrix for the first image, and adapted to compute an area shift vector for each area of the spatial matrix for the first image.

54. The medical imaging system of claim 53, wherein the edge-strength-based routine comprises an area vector selection routine adapted to select one shift vector of the plurality of possible shift vectors in a maximum shift search range for the area that provides a minimum total edge strength for the area.

55. A system for decomposing soft tissue and bone images from first and second energy images acquired by a digital radiography imaging system, comprising:
  means for warpingly registering the first energy image to the second energy image prior to image decomposition; and
  means for decomposing the soft tissue and bone images from the first and second energy images.

56. The system of claim 55, comprising means for acquiring the first and second energy images from the digital radiography imaging system.

* * * * *